US009096845B2

(12) United States Patent
Kuhn et al.

(10) Patent No.: US 9,096,845 B2
(45) Date of Patent: Aug. 4, 2015

(54) ENCAPSULATION OF BACTERIA AND VIRUSES IN ELECTROSPUN FIBERS

(75) Inventors: Jonathan Charles Kuhn, Haifa (IL); Eyal Zussman, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1111 days.

(21) Appl. No.: 11/896,130

(22) Filed: Aug. 29, 2007

(65) Prior Publication Data

US 2009/0061496 A1 Mar. 5, 2009

(51) Int. Cl.

| | |
|---|---|
| ***C12N 11/00*** | (2006.01) |
| ***C12N 11/04*** | (2006.01) |
| ***C12N 1/20*** | (2006.01) |
| ***C12N 7/00*** | (2006.01) |
| ***C12N 11/14*** | (2006.01) |
| ***A61K 9/00*** | (2006.01) |
| ***C12N 1/04*** | (2006.01) |
| ***C12N 13/00*** | (2006.01) |
| ***D01D 5/00*** | (2006.01) |
| ***D01F 1/10*** | (2006.01) |

(52) U.S. Cl.

CPC .............. *C12N 11/00* (2013.01); *A61K 9/0092* (2013.01); *C12N 1/04* (2013.01); *C12N 1/20* (2013.01); *C12N 7/00* (2013.01); *C12N 11/04* (2013.01); *C12N 11/14* (2013.01); *C12N 13/00* (2013.01); *D01D 5/0007* (2013.01); *D01F 1/10* (2013.01)

(58) Field of Classification Search

USPC ........... 435/173.1, 173.9, 174, 176, 177, 180, 435/182, 260

See application file for complete search history.

(56) References Cited

U.S. PATENT DOCUMENTS

| | | | | |
|---|---|---|---|---|
| 4,921,475 | A | 5/1990 | Sibalis | |
| 5,209,734 | A | 5/1993 | Hurley et al. | |
| 5,688,501 | A * | 11/1997 | Merril et al. | 424/93.6 |
| 5,795,340 | A | 8/1998 | Lang | |
| 6,537,195 | B2 | 3/2003 | Forman | |
| 6,537,241 | B1 | 3/2003 | Odland | |
| 7,066,922 | B2 | 6/2006 | Angel et al. | |
| 2001/0014394 | A1 | 8/2001 | Soane et al. | |
| 2001/0034503 | A1 | 10/2001 | Mehier | |
| 2003/0098518 | A1 | 5/2003 | Averdung et al. | |
| 2003/0135158 | A1 | 7/2003 | Gonnelli | |
| 2003/0139727 | A1 | 7/2003 | Angel et al. | |
| 2004/0018226 | A1* | 1/2004 | Wnek et al. | 424/443 |
| 2004/0030377 | A1 | 2/2004 | Dubson et al. | |
| 2004/0147903 | A1 | 7/2004 | Latini | |
| 2004/0223954 | A1* | 11/2004 | Bruessow et al. | 424/93.6 |
| 2005/0180992 | A1* | 8/2005 | Belcher et al. | 424/204.1 |
| 2006/0119015 | A1 | 6/2006 | Wehrspohn et al. | |
| 2006/0200232 | A1 | 9/2006 | Phaneuf et al. | |
| 2006/0226580 | A1 | 10/2006 | Xia et al. | |
| 2006/0228435 | A1 | 10/2006 | Andrady et al. | |
| 2010/0129656 | A1 | 5/2010 | Zussman et al. | |
| 2010/0303881 | A1 | 12/2010 | Hoke et al. | |
| 2011/0081394 | A1 | 4/2011 | Zussman et al. | |

FOREIGN PATENT DOCUMENTS

| | | |
|---|---|---|
| AU | 2007303821 | 4/2008 |
| CN | 1799649 | 7/2006 |
| EP | 2079860 | 7/2009 |
| WO | WO 03/000381 | 1/2003 |
| WO | WO 2006/019293 | 2/2006 |
| WO | WO 2006/108809 | 10/2006 |
| WO | WO 2008/041183 | 4/2008 |
| WO | WO 2009/104174 | 8/2009 |
| WO | WO 2009/104175 | 8/2009 |
| WO | WO 2009/104176 | 8/2009 |

OTHER PUBLICATIONS

Salalha, W et al. Encapsulation of bacteria and viruses in electrospun nanofibres. Nanotechnology. 2006. 17: 4675-4681. Published Aug. 30, 2006.*

Theron, A et al. Electrostatic field-assisted alignment of electrospun nanofibres. Nanotechnology. 2001. 12: 384-390.*

Lee, S et al. Virus-based fabrication of micro- and nanofibers using electrospinning. Nano Letters. Mar. 2004. 4(3): 387-390.*

Zussman, E et al. Formation of nanofiber crossbars in electrospinning. Applied Physics Letters. 2003. 82(6): 973-975.*

Interantional Preliminary Report on Patentability Dated Sep. 2, 2010 From the International Bureau of WIPO Re. Application No. PCT/IL2009/000171.

International Preliminary Report on Patentability Dated Sep. 2, 2010 From the International Bureau of WIPO Re.: Application No. PCT/IL2009/000169.

International Preliminary Report on Patentability Dated Sep. 2, 2010 From the International Bureau of WIPO Re.: Application No. PCT/IL2009/000170.

International Preliminary Report on Patentability Dated Apr. 16, 2009 From the International Bureau of WIPO Re.: Application No. PCT/IB2007/054001.

(Continued)

*Primary Examiner* — Allison Fox
*Assistant Examiner* — Susan E Fernandez

(57) ABSTRACT

A method of preserving organisms in viable form, the method comprising: suspending organisms in a solution of electrospinnable polymer; drawing droplets of said solution through a spinneret; applying an electrostatic field to said droplets under electrospinning conditions; so as to form fibers having a diameter no greater than about 5 μm within which distinct organisms are encapsulated in viable form.

25 Claims, 8 Drawing Sheets

(56) References Cited

OTHER PUBLICATIONS

International Search Report and the Written Opinion Dated Sep. 29, 2009 From the International Searching Authority Re.: Application No. PCT/IL2009/000169.
International Search Report and the Written Opinion Dated Sep. 29, 2009 From the International Searching Authority Re.: Application No. PCT/IL2009/000171.
International Search Report and the Written Opinion Dated Sep. 30, 2009 From the International Searching Authority Re.: Application No. PCT/IL2009/000170.
International Search Report Dated Oct. 14, 2008 From the International Searching Authority Re.: Appliation No. PCT/IB2007/054001.
Translation of Office Action Dated Oct. 13, 2010 From the State Intellectual Property Office of the People's Republic of China Re. Application No. 200780044536.1.
Written Opinion Dated Oct. 14, 2008 From the International Searching Authority Re.: Application No. PCT/IB2007/054001.
Bognitzki et al. "Polymer, Metal, and Hybrid Nano- and Mesotubes by Coating Degradable Polymer Template Fibers (TUFT Process)", Advanced Materials, 12(9): 637-640, 2000.
Caruso et al. "Titanium Dioxide Tubes From Sol-Gel Coating of Electrospun Polymer Fibers", Advanced Materials, 13: 1577-1579, Oct. 16, 2001.
Dror et al. "One-Step Production of Polymeric Microtubes by Co-Electrospinning", Small, XP002497054, 3(6): 1064-1073, Jun. 4, 2007.
Dror et al. "Viable Encapsulation of Enzymes in Biodegradable Tubular Structures", Faculty of Mechanical Engineering, Faculty of Biology, Technion Israel Institute of Technology, Haifa, IL, 18 P.
He et al. "Recent Development of the Nanocomposites Prepared by Coaxial Jet Technology", Acta Materiae Compositae Sinica, 22(6): 1-8, Dec. 2005. Abstract in English.
Huang et al. "Encapsulating Drugs in Biodegradable Ultrafine Fibers Through Co-Axial Electrospinning", Journal of Biomedical Materials Research, Part A, 77A: 169-179, 169, 2006.
Jiang et al. "A Facile Technique to Prepare Biodegradable Coaxial Electrospun Nanofibers for Controlled Release of Bioactive Agents", Journal of Controlled Release, XP005163067, 108(2-3): 237-243, Nov. 28, 2005.
Jiang et al. "Modulation of Protein Release From Biodegradable Core-Shell Structured Fibers Prepared by Coaxial Electrospinning", Journal of Biomedical Materials Research Part B: Applied Biomaterials, 79B: 50-57, 2006.
Li et al. "Direct Fabrication of Composite and Ceramic Hollow Nanofibers by Electrospinning", Nano Letters, 4(5): 933-938, 2004.
Li et al. "Electrospinning of Nanofibers: Reinventing the Wheel?", Advanced Materials, 16(14): 1151-1170, Jul. 19, 2004.
Li et al. "Electrospinning: A Simple and Versatile Technique for Producing Ceramic Nanofibers and Nanotubes", Journal of the American Ceramic Society, 89(6): 1861-1869, 2006.
Li et al. "Porous Ultrafine Nanofibers Having a Ultrahigh Specific Surface Area", Chinese Science Bulletin, 49(21): 2160-2163, Nov. 2004. Chinese Only!
Li et al. "Use of Electrospinning to Directly Fabricate Hollow Nanofibers With Functionalized Inner and Outer Surfaces", Small, XP002497053, 1(1): 83-86, Jan. 1, 2005.
Loscertales et al. "Electrically Forced Coaxial Nanojets for One-Step Hollow Nanofiber Design", Journal of the American Chemical Society, JACS, 126: 5376-5377, 2004.
Loscertales et al. "Micro/Nano Encapsulation via Electrified Coaxial Liquid Jets", Science, 295: 1695-1698, Mar. 16, 2002.
Reneker et al. "Electrospinning of Nanofibers From Polymer Solutions and Melts", Advances in Applied Mechanics, 41: 1-3, 103-115, 142-153, 2006.
Reznik et al. "Evolution of a Compound Droplet Attached to a Core-Shell Nozzle Under the Action of a Strong Electric Field", Physics of Fluids, 18: 062101-1-062101-13, 2006.
Salalha et al. "Encapsulation of Bacteria and Viruses in Electrospun Nanofibres", Nanotechnology, 17: 4675-4681, 2006.
Sun et al. "Compound Core-Shell Polymer Nanofibers by Co-Electrospinning", Advanced Materials, XP002497055, 15(22: 1929-1932, Nov. 17, 2003.
Xie et al. "Ultra-High Surface Fibrous Membranes From Electrospinning of Natural Proteins: Casein and Lipase Enzyme", Journal of Materials Science, 38: 2125-2133, 2003.
Yarin et al. "Material Encapsulation and Transport in Core-Shell Micro/Naonofibers, Polymer and Carbon Nanotubes and Micro/Nanochannels", Journal of Materials Chemistry, XP002546457, 17(25): 2585-2599, Jul. 1, 2007. Chapter III Section (ii).
Yu et al. "Production of Submicrometer Diameter Fibers by Two-Fluid Electrospinning", Advanced Materials, 16(17): 1562-1566, Sep. 3, 2004.
Zhang et al. "Coaxial Electrospinning of (Fluorescein Isothiocyanate-Conjugated Bovine Serum Albumin)-Encapsulated Poly(ϵ-Caprolactone) Nanofibers for Sustained Release", Biomacromolecules, 7(4): 1049-1057, 2006.
Zussman et al. "Electrospun Polyacrylonitrile/Poly(Methyl Methacrylate)-Derived Turbostratic Carbon Micro-/Nanotubes", Advanced Materials, 18: 348-353, 2006.
Response Dated Mar. 24, 2011 to Office Action of Oct. 13, 2010 From the State Intellectual Property Office of the People's Republic of China Re. Application No. 200780044536.1.
Larsson et al. "Detection of Number and Viability of *E. coli* and *A. hydrophila* With FISH Technique", Techneau, D.3.5.3, p. 1-30, Apr. 30, 2008.
Restriction Official Action Dated May 9, 2012 From the US Patent and Trademark Office Re. U.S. Appl. No. 12/918,372.
Official Action Dated Jun. 18, 2013 From the US Patent and Trademark Office Re. U.S. Appl. No. 12/918,365.
Translation of Office Action Dated Jun. 4, 2013 From the State Intellectual Property Office of the People's Republic of China Re. Application No. 200780044536.1.
Official Action Dated Aug. 27, 2012 From the US Patent and Trademark Office Re. U.S. Appl. No. 12/311,601.
Communication Pursuant to Article 94(3) EPC Dated Aug. 23, 2013 From the European Patent Office Re. Application No. 09713280.7.
Official Action Dated Sep. 6, 2013 From the US Patent and Trademark Office Re. U.S. Appl. No. 12/918,372.
Patent Examination Report Dated Nov. 19, 2012 From the Australian Government, IP Australia Re. Application No. 2007303821.
Official Action Dated Feb. 7, 2013 From the US Patent and Trademark Office Re. U.S. Appl. No. 12/311,601.
Translation of Office Action Dated Mar. 1, 2012 From the State Intellectual Property Office of the People's Republic of China Re. Application No. 200780044536.1.
Applicant-Initiated Interview Summary Dated Apr. 30, 2014 From the US Patent and Trademark Office Re. U.S. Appl. No. 12/918,372.
Advisory Action Before the Filing of an Appeal Brief Dated May 16, 2013 From the US Patent and Trademark Office Re. U.S. Appl. No. 12/311,601.
Advisory Action Before the Filing of an Appeal Brief Dated May 30, 2014 From the US Patent and Trademark Office Re. U.S. Appl. No. 12/918,365.
Requisition by the Examiner Dated May 22, 2014 From the Canadian intellectual Property Office Re. Application No. 2,664,972.
Advisory Action Before the Filing of an Appeal Brief Dated Apr. 12, 2013 From the US Patent and Trademark Office Re. U.S. Appl. No. 12/311,601.
Official Action Dated Apr. 8, 2013 From the US Patent and Trademark Office Re. U.S. Appl. No. 12/918,377.
Communication Pursuant to Article 94(3) EPC Dated Jul. 18, 2012 From the European Patent Office Re. Application No. 09713280.7.
Communication Pursuant to Article 94(3) EPC Dated Jul. 19, 2012 From the European Patent Office Re. Application No. 09712148.7.
Communication Pursuant to Article 94(3) EPC Dated Jul. 19, 2012 From the European Patent Office Re. Application No. 09713264.1.
Official Action Dated Aug. 8, 2012 From the US Patent and Trademark Office Re. U.S. Appl. No. 12/918,372.
Communication Under Rule 71(3) EPC Dated Dec. 10, 2013 From the European Patent Office Re. Application No. 09712148.7.

(56) References Cited

OTHER PUBLICATIONS

Office Action Dated Nov. 21, 2013 From the State Intellectual Property Office of the People's Republic of China Re. Application No. 200780044536.1 and Its Translation Into English.
Official Action Dated Jan. 17, 2014 From the US Patent and Trademark Office Re. U.S. Appl. No. 12/918,365.
Official Action Dated Mar. 11, 2013 From the US Patent and Trademark Office Re. U.S. Appl. No. 12/918,372.
Kim et al. "Controlled Protein Release From Electrospun Biodegradable Fiber Mesh Composed of Poly(Epsilon-Caprolactone) and Poly(Ethylene Oxide)", International Journal of Pharmaceutics, 338: 276-283, 2007.
Zhang et al. "Biomimetic and Bioactive Nanofibrous Scaffolds From Electrospun Composite Nanofibers", International Journal of Nanomedicine, 2(4): 623-638, 2007.
Official Action Dated Jun. 20, 2012 From the US Patent and Trademark Office Re. U.S. Appl. No. 12/918,377.
Decision to Grant a European Patent Pursuant to Article 97(1) EPC Dated Jul. 11, 2013 From the European Patent Office Re. Application No. 07826621.0.
Dror et al. "Encapsulation of Enzymes in Biodegradable Tubular Structures", Macromolecules, 41(12): 4187-4192, May 24, 2008.
Communication Pursuant to Article 94(3) EPC Dated Aug. 20, 2013 From the European Patent Office Re. Application No. 09713264.1.
Communication Pursuant to Article 94(3) EPC Dated Dec. 2, 2011 From the European Patent Office Re. Application No. 07826621.0.
International Preliminary Report on Patentability Dated Sep. 2, 2010 From the International Bureau of WIPO Re. Application No. PCT/IL2009/000171.
Official Action Dated Feb. 14, 2012 From the US Patent and Trademark Office Re. U.S. Appl. No. 12/311,601.
Restriction Official Action Dated Dec. 23, 2011 From the US Patent and Trademark Office Re. U.S. Appl. No. 12/311,601.
Li et al. "Nano-Porous Ultra-High Specific Surface Ultrafine Fibers", Chinese Science Bulletin, 49(22): 2368-2371, Nov. 2004.
Zhang et al. "Coaxial Electrospinning of (Fluorescein Isothiocyanate-Conjugated Bovine Serum Albumin)-Encapsulated Poly(?-Caprolactone) Nanofibers for Sustained Release", Biomacromolecules, 7(4): 1049-1057, 2006.
Translation of Office Action Dated Dec. 4, 2012 From the State Intellectual Property Office of the People's Republic of China Re. Application No. 200780044536.1.
Restriction Official Action Dated Mar. 1, 2013 From the US Patent and Trademark Office Re. U.S. Appl. No. 12/918,365.
Official Action Dated Feb. 5, 2015 From the US Patent and Trademark Office Re. U.S. Appl. No. 12/918,372.
Official Action Dated Feb. 4, 2015 From the US Patent and Trademark Office Re. U.S. Appl. No. 12/918,365.
Requisition by the Examiner and Examination Search Report Dated Jan. 23, 2015 From the Canadian Intellectual Property Office Re. Application No. 2,664,972.
Official Action Dated Jan. 9, 2015 From the US Patent and Trademark Office Re. U.S. Appl. No. 12/918,377.
Official Action Dated Jan. 14, 2015 From the US Patent and Trademark Office Re. U.S. Appl. No. 12/311,601.
McCann et al. "Electrospinning of Nanofibers With Core-Sheath, Hollow, or Porous Structures", Journal of Materials Chemistry, 15: 735-738, 2005.

* cited by examiner (a) (b)

(c) (d)

ENCAPSULATION OF BACTERIA AND VIRUSES IN ELECTROSPUN FIBERS

FIELD OF THE INVENTION

The present invention relates to the field of preservation of organisms, and more particularly to encapsulation of viable bacteria and non-filamentous viruses in electrospun fibers.

BACKGROUND OF THE INVENTION

Bacteria are utilized in a wide range of commercial applications. For example, lactic acid bacteria cultures are used to produce cheese, yogurt, and other dairy products. *Lactobacillus acidophilus, Bifidobacteria, E. coli* and other types of bacteria are extensively used as probiotics. Live attenuated bacteria are extensively used to vaccinate different domestic animals and humans. Genetically altered bacteria are widely used as expression hosts for a variety of proteins and products.

Bacterial viruses (bacteriophages) may be used as an alternative to anti-bacterial antibiotics (phage therapy) and as vectors for gene delivery (viral and non-viral vectors) [1-3], which uses require that the bacterial viruses are delivered to a desired destination in an intact and viable form.

Bacteria can be preserved in a dry form, e.g. by lyophilization, or in a wet form as concentrated cells. Wet storage preserves bacterial cells only for a relatively short period. On the other hand, bacteriophages can sometimes be preserved in liquid form for relatively long periods, depending on the type of virus preserved.

Dry form storage has the advantages of reduced weight and requires reduced space for storage. Room temperature storage of dried materials is moreover cost effective when compared to low temperature storage options and the concomitant cost. However, lyophilization leads to loss of viability, loss of virulence and occurrence of mutations with many bacterial strains, and the vial in which the bacteria are stored cannot be resealed after opening, such that any remaining material must be discarded. Lyophilization is not suitable for phage therapy.

The preservation and storage of biologically active materials in dry form, while maintaining its activity, is important for many applications in the food and microbiological industries, agriculture, medical and research purposes.

There is thus a widely recognized need for, and it would be highly advantageous to have, a method of preserving bacteria and non-filamentous viruses in viable form.

SUMMARY OF THE INVENTION

According to one aspect of the present invention there is provided a method of preserving organisms in viable form, the method comprising suspending organisms in a solution of an electrospinnable polymer, drawing droplets of the solution through a spinneret, and applying an electrostatic field to the droplets under electrospinning conditions; thereby forming fibers having a diameter no greater than about 5 μm within which distinct organisms are encapsulated in viable form.

According to a further aspect of the present invention, there is provided a fibrous material encapsulating bacteria or non-filamentous viruses in viable form, wherein the fibrous material is formed by suspending bacteria or non-filamentous viruses in a solution of electrospinnable polymer; drawing droplets of the solution through a spinneret; and applying an electrostatic field to the droplets under electrospinning conditions, thereby forming fibers comprising said bacteria or non-filamentous viruses.

According to further features in embodiments of the present invention, the biological matter is optionally selected from the group consisting of bacteria and non-filamentous viruses, such as, for example, *Escherichia coli* or *Staphylococcus* albus bacteria, or bacterial viruses T7, T4, and λ, or animal viruses such as Herpes simplex, Cytomegalovirus, Papilloma virus, Adenovirus, Burkitt lymphoma virus, Arbovirus, Arenavirus, Epstein-Barr virus, Varicella virus, Comavirus, Coxsackievirus, Eboli virus, Enterovirus, Hepatitis virus, Influenza virus, Marburg virus, Measles virus, Mumps virus, Polio virus, Rhinovirus, Rubella virus, Smallpox virus, Rabies virus, and Rotavirus. Viruses are optionally grown on *E. coli* strains, such as for example, strain K12 or on other suitable hosts.

According to yet further features in embodiments of the present invention, the solution further comprises an osmolarity-regulating agent, such as, for example, glycerol, sugar (including but not limited to sucrose, glucose, fructose, lactose and the like) Ficoll®, glycol, polyethylene glycol, and sugar-alcohols, such as mannitol, inositol, xylitol, and adonitol, amino acids such as glycine and arginine, biological polymeric molecules and proteins such as albumin. Optionally and preferably, the osmolarity-regulating agent is selected from the group consisting of glycerol, a polysaccharide polymer, glycol, and polyethylene glycol.

According to further features in embodiments of the present invention, the spinneret is optionally a pipette or a syringe. The syringe may optionally further comprise a needle and a syringe pump. The needle may optionally have an inner diameter of from about 0.1 to about 2 mm.

According to still further features in embodiments of the present invention, the electrospinnable polymer may optionally be selected from the group consisting of polyamides, poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) poly(acrylic acid), poly(vinyl acetate), polyacrylamide, poly(ethylene-co-vinyl acetate), poly(ethylene glycol), poly(methacrylic acid), polylactides, polyglycolides, poly (lactide-co-glycolides), polyanhydrides, polyorthoesters, poly(carbonate), poly(acrylo nitrile), poly(ethylene oxide), polyaniline, polyvinyl carbazole, polystyrene, poly(vinyl phenol), polyhydroxyacids, poly(caprolactone), polyanhydrides, polyhydroxyalkanoates, polyurethanes, collagen, albumin, alginate, chitosan, starch, hyaluronic acid, and blends and copolymers thereof.

Optionally and preferably, the electrospinnable polymer comprises polyvinyl alcohol.

According to further features in embodiments of the present invention, the step of applying an electrostatic field comprises inserting a first electrode in the spinneret, positioning a counterelectrode at a distance (such as, for example 20 cm) from the first electrode and applying a high voltage (preferably up to about 30 kV) between the first electrode and the counterelectrode.

Optionally and preferably, the first electrode is formed from copper and the counterelectrode is formed from aluminum.

According to further features in embodiments of the present invention, the counterelectrode is a collector for said fibers, and may comprise for example, a rotating disc. Optionally, the disc may be provided with a tapered edge. Further optionally, the disc may be provided with a collecting table configured to rotate about the z-axis, such that the method further comprises the step of periodically rotating the table by a predetermined number of degrees about the z-axis, wherein a mat comprising layers of fibers is formed.

According to further features in embodiments of the present invention, the method of the present invention is provided for use in phage therapy, storage of culture collections, production of biosensors, wound treatment, preparation of animal feed, storage of probiotics, vaccine preparation, preservation of genetically altered bacteria or production of a mat comprising a fibrous material encapsulating bacteria or non-filamentous viruses in viable form.

In any of the uses of the present invention, the organisms may optionally comprise live attenuated bacteria or viruses. Also optionally, genetically altered bacteria for use in the present invention may be expression hosts for proteins or vectors for gene delivery.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows an electrospinning device;

FIG. 2 is a high-resolution scanning electron micrograph of a mat formed by electrospun PVA fibers in accordance with the principles of the present invention;

FIG. 3 is a schematic illustration of rod like bacteria during the electrospinning process;

FIG. 4 shows HRSEM micrographs of individual *S. albus* cells (FIG. 4*a*) and embedded *S. albus* cells in PVA nanofibers (FIGS. 4*b*-4*d*);

FIG. 5 shows HRSEM micrographs of individual *E. coli* cells (FIG. 5*a*) and embedded *E. coli* cells in PVA nanofibers (FIGS. 5*b*-5*d*);

FIG. 6 is a fluorescent microscopy image of *E. coli* cells embedded in PVA nanofibers;

Figure 7:
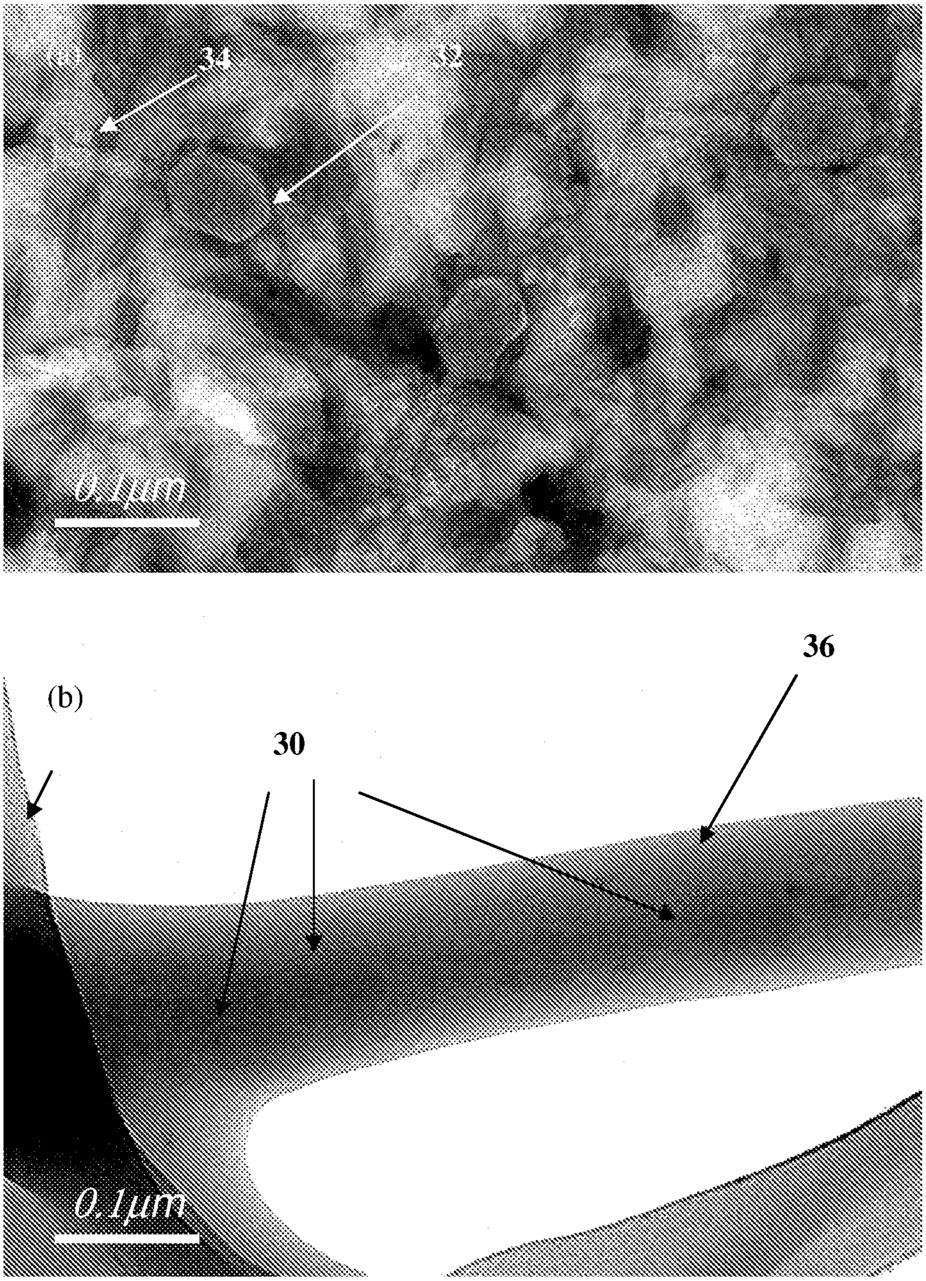
Figure 8:
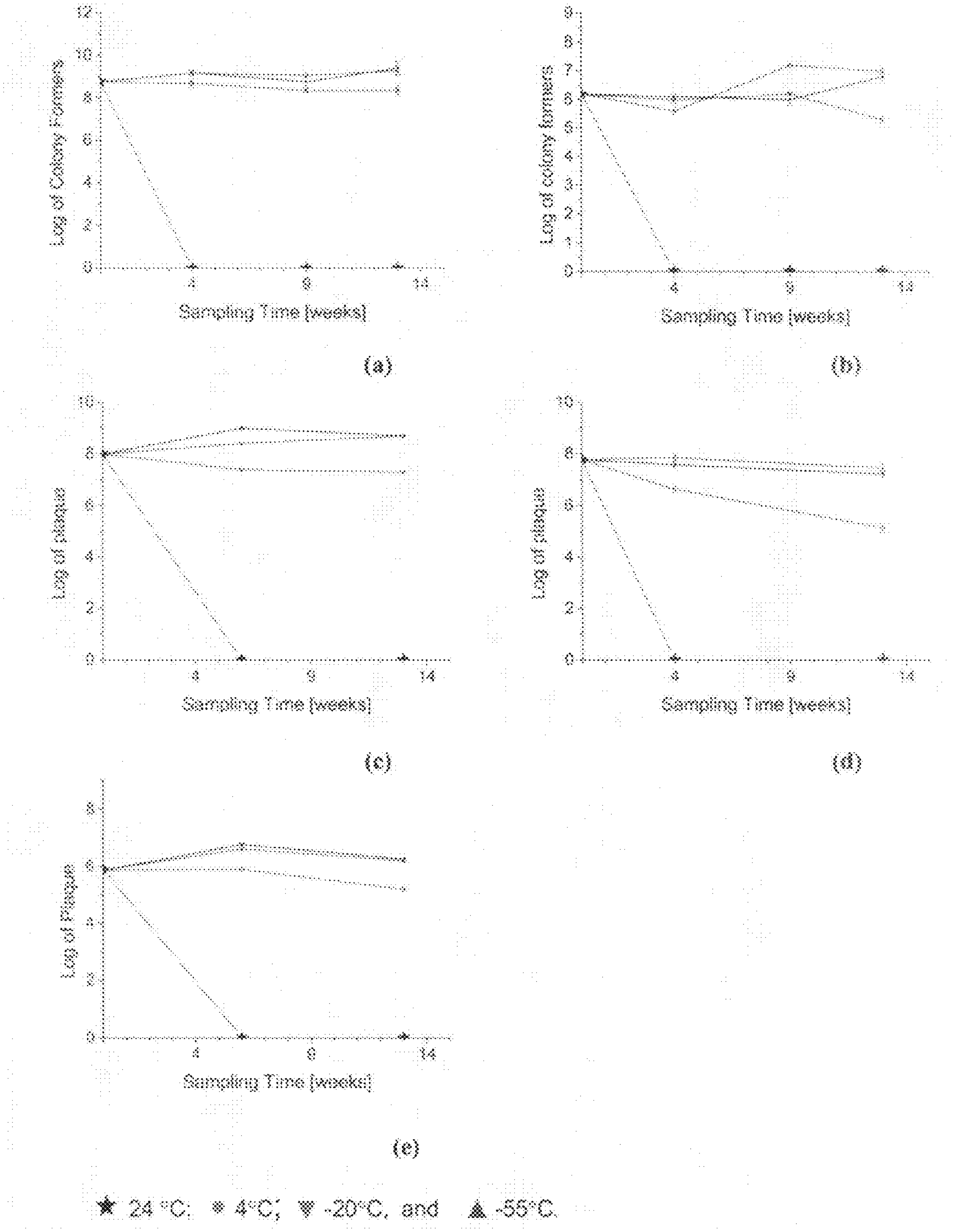

FIG. 7 shows TEM micrographs of embedded stained (FIG. 7*a*) and unstained (FIG. 7*b*) T4 bacterial viruses; and FIG. 8 presents semilog plots of the number of colony or plaque forming units per milligram of electrospun nanofibers versus sampling time at four different temperatures for *S. albus* cells (FIG. 8*a*); *E. coli* cells (FIG. 8*b*); T4 (FIG. 8*c*); T7 (FIG. 8*d*); and λ (FIG. 8*e*).

DESCRIPTION OF THE PREFERRED EMBODIMENTS

The present invention is of a method of preserving organisms such as bacteria or non-filamentous viruses in viable form by encapsulation in nanofibers produced by electrospinning. The present inventors have surprisingly found that these microorganisms are able to withstand the forces exerted during electrospinning, and remain viable during the encapsulation process.

Nanofibers are fibers with diameters varying from less than 10 nm to about 1 μm in diameter.

Biological material has been previously encapsulated in electrospun nanofibers. For example, DNA has been encapsulated for potential therapeutic applications in gene therapy [4]. It was found that plasmid DNA released directly from the electrospun scaffold was intact, capable of transforming cells, and still encoded the alpha portion of the enzyme β-galactosidase. Some proteins, enzymes and small molecules have also been embedded in electrospun nanofibers [5-9]. These studies did not teach or suggest the encapsulation of intact microorganisms in nanofibers.

U.S. Patent Application No. 20050180992 (also ref. [10]) teaches fabrication of virus-based nanofibers using wet-spinning and electrospinning processes. This application refers only to the use of filamentous M13 viruses, wherein viral fibers blended with PVP are spun into continuous uniform blended virus-PVP fibers. M13 and related filamentous viruses have very simple structures in which coat proteins are arranged helically. The use of electrospun polymer fibers for encapsulation of more complex non-filamentous viruses, having a capsid and a tail is not taught. Such complex viruses would not be expected to withstand forces exerted during electrospinning. Furthermore, no data were presented as to the numbers of infective particles before and after spinning and whether infectivity is preserved in this spun material, as well as the overall storage stability of such electrospun material. This is obviously important for the use of such material for phage therapy.

The present invention encapsulates distinct organisms within polymer nanofibers, rather than forming nanofibers in which viral fibers and polymer are uniformly blended. Furthermore, the present inventors have demonstrated storage stability of the resultant electrospun material. The present inventors have also demonstrated efficacy of the taught method for viruses having complex structures.

U.S. Patent Application Nos. 20040018226 and 20020081732 teach compositions comprising an electroprocessed material and a substance, which may be a cell. The viability of the cell in such a composition is not addressed in these applications. Examples of encapsulation of cells relate to yeast cells and mammalian cells, but encapsulation of less resilient bacterial or viral cells is not taught.

U.S. Patent Application No. 20030054035 teaches a cell storage and delivery system which include a biodegradable and/or bioabsorbable fibrous matrix physically associated with viable cells to contain and release the cells at a controlled rate. The biodegradable and/or bioabsorbable matrix can be formed by electrospinning fibers of biodegradable and/or bioabsorbable fiberizable material. Encapsulation is achieved by forming a highly porous scaffold structure within which the cells are sandwiched, rather than being encapsulated within electrospun fibers themselves, which would clearly subject the cells to high pressure. The cells described in this application are tissue precursor cells. Encapsulation of bacterial cells or viruses is not taught.

U.S. Patent Application No. 20040037813 teaches use of electroprocessed collagen, including use as an extracellular matrix and, together with cells, its use in forming engineered tissue. Encapsulation of bacteria or viruses in electrospun nanofibers is not taught.

Electrospinning involves pulling a liquid jet of a polymer solution from the tip of a droplet by electrostatic forces, such that nanofibers are formed [11-13].

An exemplary standard device for electrospinning comprises a spinneret, a high-voltage power supply, and a grounded collector [14]. The organisms are suspended in a solution of an electrospinnable polymer. The solution containing the organisms is loaded into the spinneret and droplets are allowed to form at the exit from the spinneret, to which an electrostatic field is applied.

The electrospinnable polymer may comprise any biologically compatible synthetic polymer, such as, for example, polyamides, poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly (vinyl alcohol) (PVA), poly(acrylic acid), poly(vinyl acetate), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, and polyorthoesters poly(carbonate), poly (acrylo nitrile), poly(ethylene oxide), polyaniline, polyvinyl carbazole, polystyrene and poly(vinyl phenol), polyhydroxyacids, poly(caprolactone), polyanhydrides, polyhydroxyalkanoates, polyurethanes, polysaccharides such as collagen, albumin, alginate, chitosan, starch, and hyaluronic acid.

The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated by reference as if set forth fully herein.

Preferably, the polymer is polyvinyl alcohol (PVA) in water. PVA may be used, for example, at a concentration in the range of from about 5% to about 15% w/w, such as, for example, about 14% w/w.

According to preferred embodiments of the present invention, an osmolarity regulating agent may form part of the solution for electrospinning. The osmolarity regulating agent optionally and preferably comprises any suitable material with high osmolarity, including but not limited to, glycerol, sugar (including but not limited to sucrose, glucose, fructose, lactose and the like) Ficoll®, glycol, polyethylene glycol, and sugar-alcohols, such as mannitol, inositol, xylitol, and adonitol, amino acids such as glycine and arginine, biological polymeric molecules and particularly proteins such as albumin. Ficoll® is a neutral, high mass and highly branched sucrose polymer, which dissolves readily in aqueous solutions, and is available from GE Healthcare.

The spinneret may comprise, for example, a pipette or a syringe fitted with a needle, such that a droplet is formed at the open tip of the needle. The syringe optionally has a volume of from about 0.1 to about 100 ml. The syringe may optionally further comprise a syringe pump, for driving the solution to the tip of the needle.

The syringe needle may have an inner diameter of from about 0.1 to about 2.0 mm. For example, a syringe of volume 1 ml, with a needle of inner diameter 0.5 mm may be used.

A pendant droplet of polymer-water solution comprising the biological organisms is suspended from the tip of the syringe. Optionally, a flow rate of 0.2-0.5 ml $h^{-1}$ is used.

An electrostatic field is applied to the droplet by immersing a first electrode in the solution, placing a counter-electrode at a selected distance from the spinneret, and applying a high voltage current of from 1 kV up to 30 kV, such as, for example, 1 kV, to the solution. The distance between the electrodes may be up to about 20 cm, such as, for example, about 12 cm. The electrode may be formed from any suitable material, such as, for example, copper or any other conducting material, preferably a metal.

The electrostatic field competes with the surface tension of the polymer solution to form a Taylor cone [15]. If the viscosity of the material is sufficiently high, immediate capillary break-up of the jet is prevented. Electrostatic forces associated with mutual Coulombic interactions at different sections of the jet make it unstable when subjected to bending perturbations [16-18]. The bending instability rearranges the jet into a sequence of connected loops, which become unstable, forming secondary and tertiary loops. The jet configuration thus assumes a complex multiloop path filling a virtual cone emerging from an almost straight initial jet segment. The length of the jet then increases enormously over a relatively short distance from its origin, resulting in a drastic reduction in diameter, to the submicron range. The group of solidifying loops is pulled towards the grounded collector, which may optionally also serve as the counter electrode where it is deposited and ultimately discharged. As this is occurring, the rapid solvent evaporation fixes the polymer matrix in this stretched, yet non-equilibrium state. This process allows for the fabrication in a single stage, and in less than 10 ms of nanofibers ranging from 100 to 1000 nm in diameter [15, 16, 19].

The nanofibers are allowed to collect until the nanofiber mat reaches a desired size, and then removed from the collector. Biological organisms in the suspension are encapsulated within the nanofibers.

The collector may comprise, for example, a rotating collector disc, which acts as an electrostatic lens that pulls the spun nanofibers to a focal point, namely the edge of the disc. The collector disc may optionally be formed of any suitable material, such as aluminium or zinc, or any other conducting material, preferably a metal or metal combination or composite. The linear speed at the edge of the disc may be in the range of from about 2 to about 20 m $s^{-1}$, such as for example about 9 m $s^{-1}$.

The relative strengths of electrostatic and surface tension forces are given by the electric Bond number $B_{OE}$. A typical electrical Bond number for the electrospinning process, close to the droplet, is of the order of $$B_{OE}=r \cdot E_x^2/\gamma=10$$

where $E_x$ is the electric field strength, which is in the order of 1 kV $cm^{-1}$ r is the jet radius, which is preferably about $10^{-3}$ cm; and $\gamma$ is the surface tension coefficient of the solution, which is preferably about 50 g $s^{-2}$.

The value of the Bond number affects the evolution of a droplet, by determining the rates of expansion and subsequent detachment of the droplet. Preferably, the Bond number is in the range of from about 1 to about 100.

Figure 1:
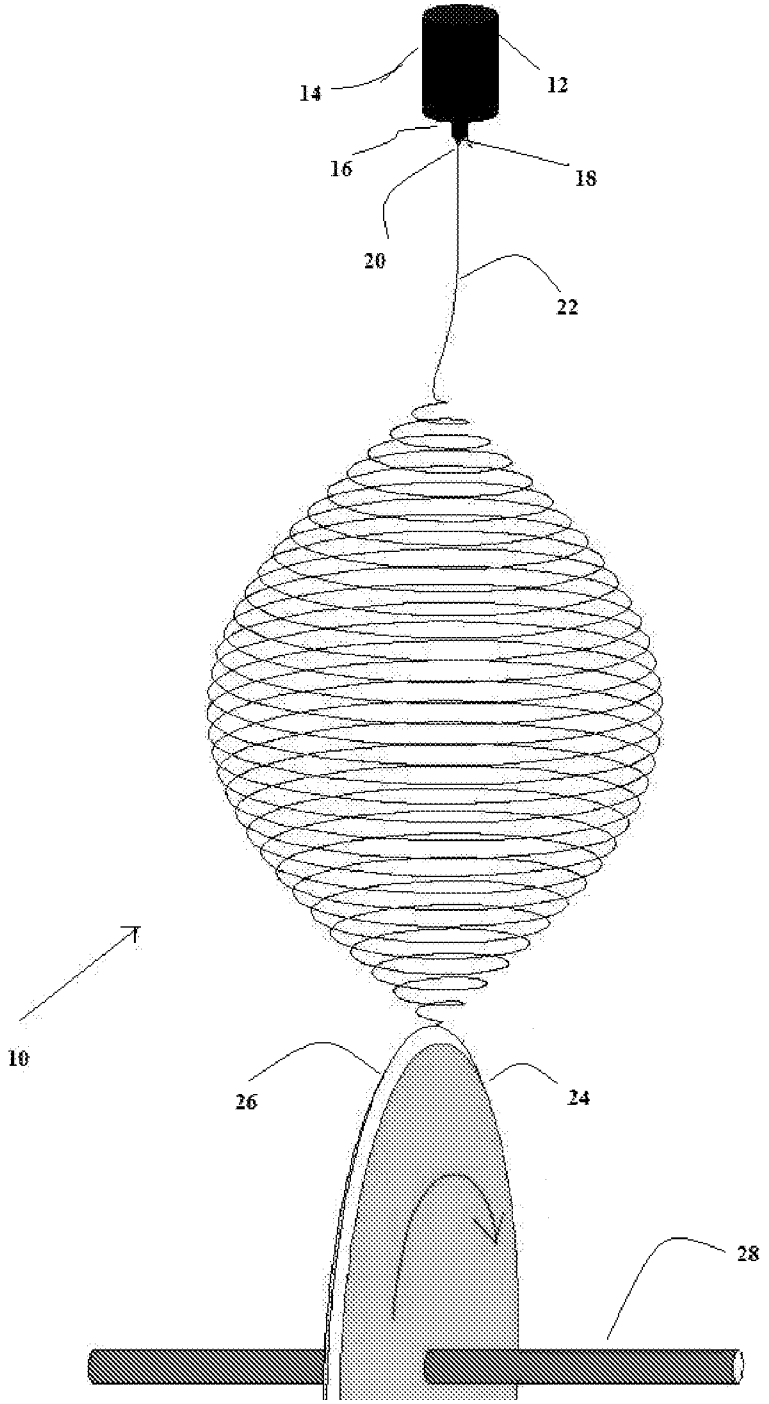

A typical electrospinning setup 10 is shown in FIG. 1. Polymer-water-biological matter solution 12 is filled into syringe 14, provided with a needle 16 having an open tip 18. Droplets 20 formed at tip 18 are subjected to an electrostatic field from a high-voltage power supply, such that a jet 22 is formed, and flows downwards towards a rotating collector disc 24, placed at a selected distance, such as about 200 mm, below droplet 20. Disc 24 is made of aluminium, having a diameter of about 200 mm. Disc 24 optionally has a tapered edge 26 in order to create a stronger converging electrostatic field. Disc 24 is optionally provided with a table (not shown) that collects the nanofibers, and which is designed to rotate about the z-axis 28. To create mats, which are layers of nanofiber arrays, each aligned at a set angle to the layer below, disc 24 is periodically stopped temporarily and the table rotated the desired number of degrees.

Figure 2:
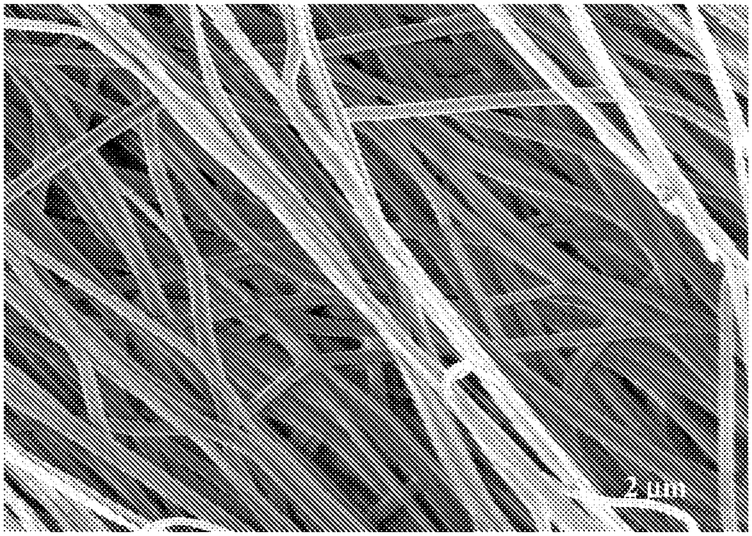

FIG. 2 shows a high-resolution scanning electron micrograph of a mat formed by electrospun PVA nanofibers.

The biological organisms may comprise, for example, whole spherical or rod-like bacterial cells or viruses.

Bacterial cells may comprise, for example, Gram negative bacteria such as *Escherichia coli* (such as the K12 strain, or derivative strain W3110), or Gram positive bacteria, such as *Staphylococcus albus*.

Viruses may comprise, for example, bacterial viruses T7, T4, and x, which are optionally grown on the K12 strain of *E. coli*. Further non-limiting examples of viruses which may be encapsulated by the method of the present invention include Herpes simplex, Cytomegalovirus, Papilloma virus, Adenovirus, Burkitt lymphoma virus, Arbovirus, Arenavirus, Epstein-Barr virus, Varicella virus, Cornavirus, Coxsackievirus, Eboli virus, Enterovirus, Hepatitis virus, Influenza virus, Marburg virus, Measles virus, Mumps virus, Polio virus, Rhinovirus, Rubella virus, Smallpox virus, Rabies virus, and Rotavirus. All of these different types of viruses are described herein as viruses with complex structure, a term which specifically excludes filamentous viruses.

Individual bacteria or viruses can be discerned within these fibers. Rod-shaped bacteria are found to line up along the length of the fiber. The bacteria or viruses are initially dispersed in the polymer solution with random orientation. As a result of the sink-like flow at the Taylor cone, rod shaped bacteria and viruses are gradually orientated mainly along the stream lines, so that aligned organisms are pulled into the jet in a uniformly orientated manner [20].

Figure 3:
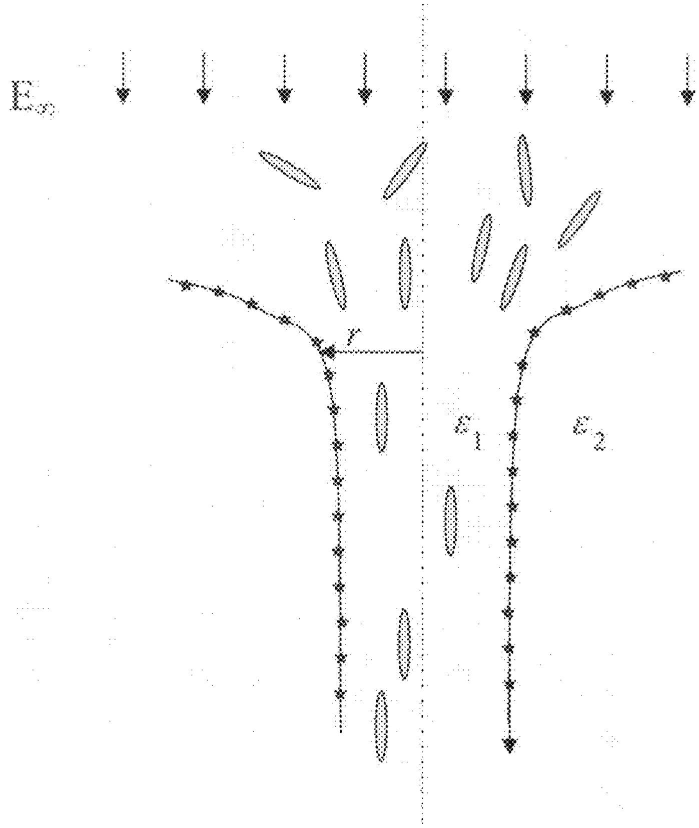

A schematic illustration of rod-like particles at the sink-like flow through a Taylor cone is presented in FIG. 3. The tangential stress, $\sigma_r$, and the normal stress, $\sigma_n$, applied to the particle are of the order of $5\times10^3$ g $cm^{-}s^{-1}$ [19]. Additional radial pressure ensues in the spun nanofibers due to surface tension, resulting in contraction of the polymer matrix. The pressure caused by surface tension forces in the case of a cylindrical fiber is $p=\gamma/r=5\times10^4$ g $cm^{-1}$ $s^{-2}$, where $\gamma$ and r are as defined above.

The results presented in the Examples section below show that viruses and bacteria can be encapsulated by electrospinning, and retain their viability in spite of the pressure buildup in the core of the nanofiber and the electrostatic field during this process.

The method of the present invention thus enables the preservation of bacterial cells and viruses in a dry and convenient form. A percentage of the bacteriophages studied (T4, T7 and $\lambda$) remained viable after electrospinning, while *S. albus* remained completely viable and *E. coli* showed a reduction in colony forming ability to 19%, which could be improved to about 50% when the cells were suspended in 5% glycerol prior to spinning. After encapsulation, all organisms retained their viability for at least 3 months, with no further loss, at −20° C. and −55° C. Therefore, encapsulation in nanofibers may provide an excellent alternative to lyophilization for the preservation of organisms.

The method has many applications in the food and microbiological industries, agriculture, medical and research purposes, including, for example, use in phage therapy, culture collections, and preservation of industrially important microorganisms (either natural or genetically engineered), such as probiotics, live attenuated bacteria and viruses for vaccine preparation (for human and veterinary vaccines), genetically altered bacteria as expression hosts for proteins and other products, and as vectors for gene delivery.

The encapsulation of the organisms within a mat of nanofibers enables selected amounts of the mat to be removed and used, without affecting the remainder of the mat.

Pieces of the mat may be placed in sample solutions, such as river water, industrial waste solutions, and used as biosensors.

Electrospun nanofiber mats can be used to conveniently cover three-dimensional surfaces (e.g. tissues and organs) and release their contents for the potential treatment of wounds and cutaneous fungal infections [8, 21-23]. For example, appropriately sized pieces of the mat comprising bacteriophages against a particular pathogenic bacterial species may be applied to wounds or external body surfaces infected with the bacterial species.

Pieces of the mat comprising bacteriophages against a particular pathogenic bacterial species may be ground up and mixed with foodstuff for feeding to animals in order to kill the specific bacterial pathogen.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

1. Materials and Methods

Biological Materials

Bacterial cells *Escherichia coli* (*E. coli*, strain W3110) [24] and *Staphylococcus* albus (*S. albus*), and bacteriophages T7 [25], T4 [26] and $\lambda$ [27] were used.

*E. coli* are rod-shaped bacilli having a diameter of about 1 μm and an average length that is twice the diameter. *E. coli* are easy to grow and to count, both microscopically and biologically. The prototrophic strain used was W3110 (obtained from R. Somerville, Purdue University, Lafayette, Ind., USA), a type K12 strain which can be grown in Vogel-Bonner medium E, comprising inorganic salts ($MgSO_4.7H_2O$, Citric acid monohydrate, $K_2HPO_4$, $NaHNH_4$ $PO_4.4H_2O$) with glucose as the carbon source [28]. Batch cultures grown overnight in this medium at 37° C. attain a density of about $1\text{-}2\times10^9$ cells $ml^{-1}$.

*S. albus* is a spherical bacterium (coccus) having a diameter of about 600 nm. The strain examined (obtained from the Department of Biological Sciences, Stanford University, Stanford, Calif.) synthesizes the restriction endonuclease SalI. This strain can be propogated in Luria-Bertani (LB) rich medium [29], which comprises tryptone, yeast extract, and NaCl. A density of about $8\times10^9$ cells $ml^{-1}$ can be reached in stationary phase cultures.

When necessary, both bacterial cultures were centrifuged, washed with Vogel-Bonner medium (without the addition of glucose), then suspended at the same density in normal strength Vogel-Bonner medium.

The cells remained highly viable for several weeks.

Bacteriophages T4, T7 and λ were grown on the K12 strain of *E. coli* and lysates were prepared on this strain in LB medium.

T4 is a bacteriophage whose icosahedral head (capsid) has a length and width of 110 nm and 85 nm, respectively, and a tail of about 130 nm length, connected to six tail fibers which are the organelles of attachment to the bacterial host [30].

The bacteriophage λ has a tail having only a single short tail fiber and a capsid of diameter about 50 nm [31].

T7 is similar to λ, but with a very short tail [25].

All three bacteriophages can easily be counted and prepared in large amounts, with more than $2\times10^{13}$ viral particles obtained from 1 liter of infected bacteria.

Electrospinning

Electrospinning was carried out by preparing a suspension of bacteria or viruses in polymer solution.

The bacteria or viruses were dispersed in LB medium. This was mixed with an equal volume of 14% w/w aqueous solution of poly(vinyl alcohol) (PVA) (Aldrich). (See Ref. [32] for electrical and rheological characterization). The suspension was subjected to electrospinning from a 1 ml syringe with a hypodermic needle having an inner diameter of 0.5 nm. The flow rate was 0.2-0.5 ml $h^{-1}$. A copper electrode was placed in the polymer solution and the suspension was spun onto the edge of a grounded collector disc. The strength of the electrostatic field was 1.1. kV $cm^{-1}$, and the distance between the electrode tip and the edge of the disc was 12 cm. The linear speed at the edge of the disc collector was V=8.8 m $s^{-1}$. All experiments were performed at room temperature (about 24° C.) and a humidity of about 50%.

Sample Preparation

As-spun nanofibers were collected on the disc edge for 1 hour, and formed a macroscopic ribbon with well-aligned nanofibers. The ribbon was detached from the disc, weighed, cut into samples, and distributed between four Eppendorf centrifuge tubes. A small sample was taken from one tube for viability tests and each of the vials was then stored at a different temperature as follows: room temperature (about 24° C.), 4° C., −20° C. and −55° C. The as-spun fibers were found to contain 7% water by weight as determined using a Speed Vac Concentrator centrifuge (Savant Corp.) with the application of both vacuum and heating (to about 40° C.) for 4 h. The samples were weighed before and after desiccation.

Viability Testing

In order to ascertain the number of living organisms in a nanofiber sample, a piece of the fibrous material was weighed. LB medium (1.0 ml) was added to the material, which was then allowed to stand at room temperature for 60 minutes, during which time the polymeric fibers dissolve completely. The cells or viruses were dispersed by agitating the solution with a Vortex mixer. The sample was then diluted in LB and assayed for bacterial cells capable of forming colonies upon incubation on LB plates containing 15 g of agar per liter, or for bacteriophage particles as determined by plaque assay.

The plaque assay was performed by mixing a dilution of the phage suspension with 0.1 ml of an overnight culture of *E. coli* strain W3110, adding 4 ml of molten top agar, and pouring this over agar plates. The plates and top layer agar contained 10 g tryptone and 5 g NaCl per liter of water; the plates contained 10 g agar, while the top layer agar contained 7 g agar per liter. All incubation steps were performed at 37° C.

Microscopy

Specimens for HRSEM and fluorescence microscopy were prepared by direct deposition of the electrospun nanofibers onto pieces of silicon wafer, which were attached to the edge of the collector disc. The micrographs were obtained by a secondary scattered-electron detector, using a Leo Gemini 982 HRSEM at an acceleration voltage of 2-4 kV and a sample-to-detector distance of 2-4 mm. Visual inspection of samples of *E. coli* containing a red fluorescent protein were performed using a Leica inverted fluorescence microscope (DMIRE 2).

Specimens for transmission electron microscopy (TEM) analysis were prepared by direct deposition of the electrospun nanofibers onto a copper grid coated by a holey carbon film. The grids were attached to the edge of the collector disc. The samples were examined using low electron-dose imaging and an acceleration voltage of 120 kV with a Philips CM 120 TEM. Images were recorded with a Gatan MultiScan 791 CCD camera, using the Gatan Digital Micrograph 3.1 software package. For TEM analysis of bacteriophage T4, the phage were negatively stained using 2% uranyl acetate. A carbon-coated grid was placed on a 10 μl sample drop of T4 for 2 minutes, blotted with filter paper, stained with 2% uranyl acetate for 2 minutes, blotted again and then air-dried.

2. Results

The electrospun nanofibers had a diameter ranging between 250 and 400 nm, and a generally uniform thickness along the nanofiber, without the formation of beads.

Figure 4:
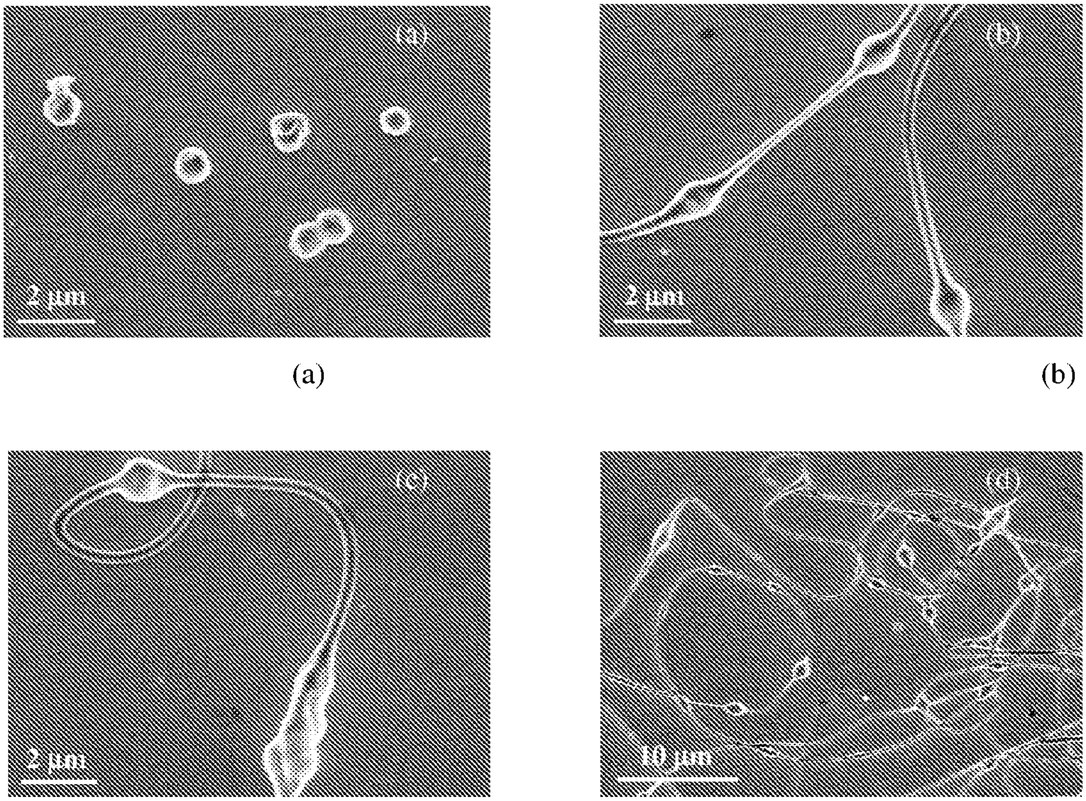

HRSEM micrographs of individual and embedded *S. albus* cells in electrospun PVA microfibers are shown in FIG. 4. FIG. 4*a* shows the individual cells. FIGS. 4*b*-4*d* show the *S. albus* cells distributed along the as-spun nanofibers, with an average distance between bacterial cells of 6±2 μm. In some places, an aggregation of cells within the nanofibers is observed (see FIG. 4*c*). Such aggregates were also observed before spinning, and it is apparent that the electrospinning process does not disrupt these aggregates. FIG. 4*d* shows a lower magnification of the cells within the fibers.

Figure 5:
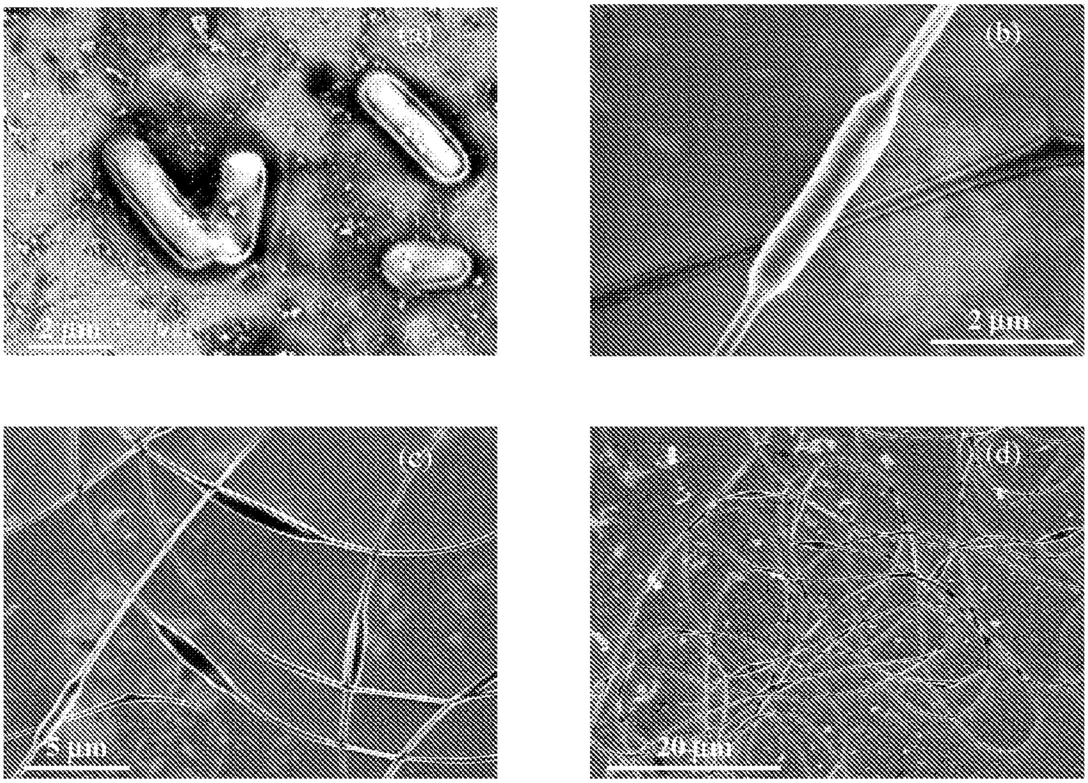

HRSEM micrographs of individual and embedded *E. coli* cells are presented in FIG. 5. The individual cells are shown in FIG. 5*a*. As shown in FIGS. 5*b*-5*d*, the polymeric matrix entirely encloses the embedded *E. coli*, resulting in a local widening of the fiber. The cells are aligned longitudinally with the nanofiber axis. The average distance between the cell centers is 10±3 μm. A lower magnification of the cells within the fibers is shown in FIG. 5*d*.

Figure 6:
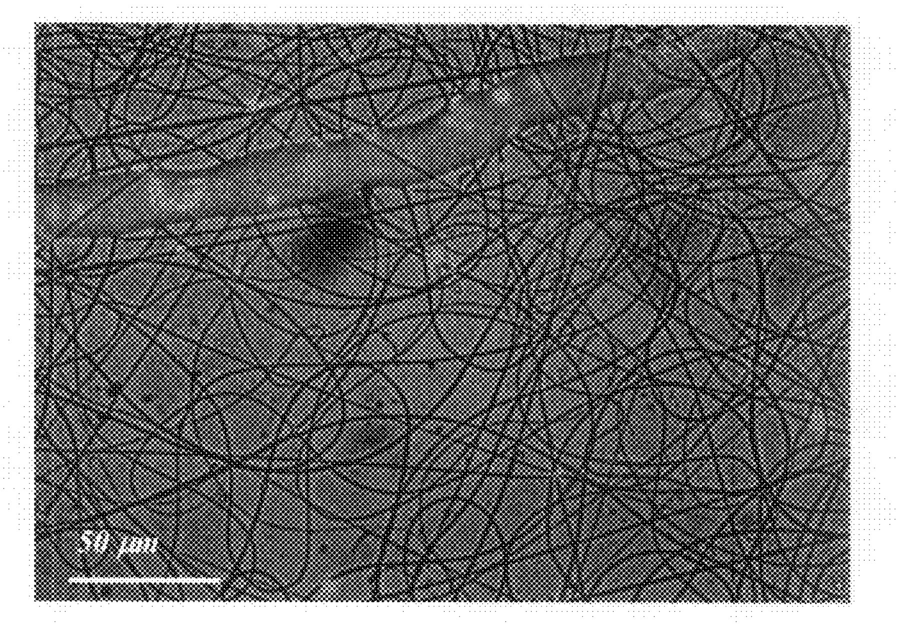

Incorporation of the *E. coli* was further demonstrated using fluorescent microscopy of fibers containing an *E. coli* strain that synthesizes a fluorescent protein, as shown in FIG. 6. This intracellular protein permits the detection of the embedded bacteria in situ. A thick fiber (>10 μm) is also found to be present among the nanofibers, as shown in the Figure. Such exceptionally thick nanofibers are apparently produced when bending instability does not take place, namely at the start and end of the electrospinning process, such that a straight, thick compound jet is deposited on the grounded collector disc.

FIG. 7 shows TEM micrographs of embedded T4 bacterial viruses. FIG. 7*a* shows three viruses 30 stained by uranyl acetate. The typical structure of a capsid 32 and a tail 34 can be clearly seen. The capsid width is about 85 nm and its length about 110 nm. The tail length is about 130 nm and its width about 20 nm. FIG. 7*b* shows three viruses 30 encapsulated inside a PVA nanofiber 36 having a diameter of about 160 nm. Due to the relatively low contrast between the polymer matrix and the unstained virus particles, the relatively thin tail cannot be seen, although the capsid is clearly observed.

In order to study the viability of the bacteria and bacteriophages before and after spinning, their ability to form colonies on agar plates (bacteria) or to form plaques on host bacteria (bacteriophages) was ascertained at each step, and then at various times after spinning. Exposure to PVA was found to have little or no effect on the viability of the two bacterial species and three types of bacteriophages studied, even when these organisms remain in the solution for several days before assaying. As shown in Table 1, the viability immediately after electrospinning was found to be 19% for *E. coli* grown on LB medium; 100% for *S. albus;* 1% for T4; 2% for T7; and 6% for λ. Both the gram positive *S. albus* and the Gram negative *E. coli* have strong cell walls and can withstand at least 50,000× the force of gravity in high speed centrifuges with no effect. The bacteriophages studied herein were found to have a surprising level of viability, since these viruses have a structure which would be expected to make them susceptible to damage during electrospinning, unlike the simple structure of filamentous viruses. While their capsids are expected to be quite resistant to physical forces (all can be subjected to forces in excess of 100,000-200,000× force of gravity), their tails and especially their tail fibers are known to be sensitive to shearing forces.

TABLE 1

Viability of electrospun bacteria and bacteriophage

| | *E. coli* | *S. albus* | T4 | T7 | Lambda |
|---|---|---|---|---|---|
| Viability (%) | 19 | 100 | 1 | 2 | 6 |

The numbers represent the relative viability (viability after spinning/viability before spinning). All organisms were suspended in LB before spinning. The sources of error are the weighing of the spun material, the dilution steps and the plating error. The total error is estimated to be between 20 and 40%.

Experiments were carried out with *E. coli* to determine whether survival during electrospinning could be improved. Cells grown in Vogel-Bonner minimal medium were found to be much more susceptible to death during the electrospinning process than those grown overnight in LB medium. Cells grown in LB medium but harvested during the logarithmic phase of growth, or grown in LB with continuous shaking for 5 days survive less well than those grown overnight in LB. A five-day-old culture was examined because *E. coli* is known to become more resistant to physical stress during cessation of growth [33].

The effect of osmolarity-regulating agents, which might overcome the fast evaporation during the electrospinning, on cell survival was studied. Cultures of *E. coli* grown in Vogel-Bonner medium, washed with 10% glucose, sucrose or glycerol and suspended in a solution of the same sugar were also examined. Glycerol provided a substantial increase in viability when the cells were subjected to electrospinning. Overnight cultures of *E. coli* were therefore grown in LB, centrifuged, and washed with 5% and 10% glycerol. The bacterial cells were then suspended in the same solution in which they were washed. Viability in 5% and 10% glycerol was found to be 48% and 22%, respectively, as shown in Table 2.

TABLE 2

Viability of *E. coli* suspended in different solutions.

| | 5% glycerol | 10% glycerol | 10% sucrose | 10% glucose |
|---|---|---|---|---|
| Viability % | 48 | 22 | 0.2 | 0.07 |

The bacteria were placed in different solutions before spinning and viability was assessed directly after spinning and compared to that before electrospinning. The numbers represent the relative viability. The sources of error are the weighing of the spun material, the dilution steps and the plating error. The total error is estimated to be between 20 and 40%.

Glycerol enters *E. coli* by facilitated diffusion, without chemical modification [34], and may protect the cells by preventing the rapid dehydration that is expected to occur as the nanofibers are generated, which may be the reason for the relatively low viability of *E. coli* in the absence of glycerol. Glyerol further protects cells during freezing by preventing formation of ice crystals which cause damage to the cell.

The evaporation of the solvent from electrospun fibers should be of the order of 10 ms. Since the mechanical stresses during electrospinning are about $5\times10^4$ g $cm^{-1}$ $s^{-2}$, which are below those which *E. coli* can withstand ($3\times10^6$ g $cm^{-1}$ $s^{-1}$) [35], this species easily survives the stresses of electrospinning. Therefore, it seems that cell death is caused by the rapid evaporation of solvent rather than by pressure.

After the organisms were embedded in fibers, they were stored at room temperature, at 4° C., −20° C. or −55° C., and the viability of the stored material was periodically examined. As shown in FIGS. 8*a* and 8*b*, both bacterial species showed a complete loss of viability after 1 month at room temperature, some loss at 4° C. over a period of 3 months (*S. albus*, FIG. 8*a*) and 4 months (*E. coli*, FIG. 8*b*), but were essentially completely stable at −20° C. and −55° C. Similar results were obtained for all three bacteriophages studied (FIGS. 8*c*-8*e*). Titers represent an average of 2 or more plates per point.

REFERENCES

[1] Barrow P A and Soothill J S *Trends in Microbiology* 1997 5 268-71
[2] Alisky J, Iczkowski K, Rapoport A and Troitsky N *Journal of Infection* 1998 36 5-15
[3] Liu F and Huang L *Journal of Controlled Release* 2002 78 259-66
[4] Luu Y K, Kim K, Hsiao B S, Chu B and Hadjiargyrou M *Journal of Controlled Release* 2003 89 341-53
[5] Zhang C X, Yuan X Y, Wu L L and Sheng J *E-Polymers* 2005
[6] Herricks T E, Kim S H, Kim J, Li D, Kwak J H, Grate J W and Xia Y N *Journal of Materials Chemistry* 2005 15 3241-45
[7] Brewster M E, Verreck C, Chun I, Rosenblatt J, Mensch J, Van Duck A, Noppe M, Arien A, Bruining M and Peeters *J Pharmazie* 2004 59 387-91
[8] Verreck C, Chun I, Rosenblatt J, Peeters J, Van Dijck A, Mensch J, Noppe M and Brewster M E *Journal of Controlled Release* 2003 92 349-60
[9] Zeng J, Aigner A, Czubayko F, Kissel T, Wendorff J H and Greiner A *Biomacromolecules* 2005 6 1484-88
[10] Lee S W and Belcher A M *Nano Letters* 2004 4 387-90
[11] Reneker D H and Chun I *Nanotechnology* 1996 7 216-23
[12] Li D and Xia Y N *Advanced Materials* 2004 16 1151-70
[13] Huang Z M, Zhang Y Z, Kotaki M and Ramakrishna S *Composites Science and Technology* 2003 63 2223-53

[14] Theron A, Zussman E and Yarin A L *Nanotechnology* 2001 12 384-90

[15] Reneker D H, Yarin A L, Fong H and Koombhongse S *Journal of Applied Physics* 2000 87 4531-47

[16] Yarin A L, Koombhongse S and Reneker D H *Journal of Applied Physics* 2001 89 3018-26

[17] Shin Y M, Hohman M M, Brenner M P and Rutledge G C *Polymer* 2001 42 9955-67

[18] Hohman M M, Shin M, Rutledge G and Brenner M P *Physics of Fluids* 2001 13 2201-20

[19] Reznik S N, Yarin A L, Zussman E and Berkovici L *Physics of Fluids* 2006 18 062101-1 to 062101-13.

[20] Dror Y, Salalha W, Khalfin R L, Cohen Y, Yarin A L and Zussman E *Langmuir* 2003 19 7012-20

[21] Verreck G, Chun I, Rosenblatt J, Peeters J, Van Dijck A, Mensch J, Noppe M and Brewster M E *Journal of Controlled Release* 2003 92 349-60

[22] Sun Z C, Zussman E, Yarin A L, Wendorff J H and Greiner A *Advanced Materials* 2003 15 1929-36

[23] Venugopal J and Ramakrishna S *Applied Biochemistry and Biotechnology* 2005 125 147-57

[24] Bachmann B J (1996) Derivations and genotypes of some mutant derivatives of *Escherichia coli* K-12 pp. 2460-2488 In *Escherichia coli and Salmonella*. F C Neidhardt, R Curtiss III, J L Ingraham, E C C Lin, K B Low, B Magasanik, W S Reznikoff, M Riley, M Schaechter, and H E Umbarger editors. ASM Press. Washington, D.C., USA

[25] Hausmann R (1988) The T7 group pp. 259-289 In *The Bacteriophages*. R Calendar editor. Plenum Press, New York and London

[26] Mosig G and Eiserling F (1988) Phage T4 structure and metabolism. pp. 521-606 In *The Bacteriophages*. R Calendar editor. Plenum Press, New York and London

[27] Brock T D (1990) *The Emergence of bacterial genetics*. pp. 179-185. Cold Spring Harbor Laboratory Press, Cold Spring Harbor, N.Y., USA

[28] Vogel H J and Bonner D M (1956) Acetylomithinase of *Escherichia coli*: partial purification and some properties. J. Biol Chem 218:97-106.

[29] Davis R W, Botstein D and Roth J R, *Advanced Bacterial Genetics*, Cold Spring Harbor Laboratory, Cold Spring Harbor, N.Y. 1980.

[30] Matthews C K, Kutter E M, Mosig G and Berget P B, *Bacteriophage T4*, American Society for Microbiology, Washington, D.C. 1983.

[31] Hendrix R W, Roberts J W, Stahl F W and Weisberg R A, *Lambda II*, Cold Spring Harbor Laboratory, Cold Spring Harbor, N.Y. 1983.

[32] Theron S A, Zussman E and Yarin A L *Polymer* 2004 45 2017-30

[33] Huisman G W, Siegele D A, Zambrano M M and Kolte R R, in: *Escherichia coli and Salmonella*, F. C. Neidhardt et al., (Eds), ASM, Washington 1987, pp. 1672-82.

[34] Maloney P C and Wilson T H, in: *Escherichia coli and Salmonella*, F. C. Neidhardt et al., (Eds), ASM, Washington 1987, pp. 1130-48.

[35] Ingraham J L and Marr A G. in: *Escherichia coli and Salmonella*, F. C. Neidhardt et al., (Eds), ASM, Washington 1987, pp. 1130-48.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of improving viability of microorganisms the method comprising:

(a) suspending the microorganisms in a solution which comprises an osmolarity-regulating agent at a concentration which reduces dehydration of said microorganisms during electrospinning as compared to dehydration of said microorganisms during electrospinning in the absence of said osmolarity regulating agent to thereby obtain a suspension comprising the microorganisms and the osmolarity-regulating agent, said microorganisms are selected from the group consisting of bacteria and non-filamentous viruses, wherein the osmolarity-regulating agent is 5% to 10% glycerol; and subsequently (b) mixing said suspension with an electrospinnable polymer to thereby obtain an electrospinnable solution; and subsequently (c) drawing droplets of said electrospinnable solution through a spinneret and applying an electrostatic field to said droplets under electrospinning conditions;

so as to form fibers having a diameter no greater than about 5 μm within which distinct microorganisms are encapsulated in viable form as assayed by colony forming ability of said bacteria, and plaque forming ability of said non-filamentous viruses, thereby improving the viability of the microorganisms as compared to the viability of said microorganisms in a fiber formed when the microorganisms are not suspended in said osmolarity-regulating agent.

2. The method of claim 1, wherein said bacteria comprise *Escherichia coli* or *Staphylococcus albus.*

3. The method of claim 1, wherein said non-filamentous viruses are selected from the group consisting of bacteriophage T7, bacteriophage T4, bacteriophage λ, Herpes simplex, Cytomegalovirus, Papilloma virus, Adenovirus, Burkitt lymphoma virus, Arbovirus, Arenavirus, Epstein-Barr virus, Varicella virus, Cornavirus, Coxsackievirus, Eboli virus, Enterovirus, Hepatitis virus, Influenza virus, Marburg virus, Measles virus, Mumps virus, Polio virus, Rhinovirus, Rubella virus, Smallpox virus, Rabies virus, and Rotavirus.

4. The method of claim 3, wherein said bacteriophage T7, T4 or λ is grown on an *E. coli* strain.

5. The method of claim 4, wherein said *E. coli* strain is K12.

6. The method of claim 1, wherein said spinneret is selected from the group consisting of a pipette and a syringe.

7. The method of claim 6, wherein said syringe further comprises a needle and a syringe pump.

8. The method of claim 7, wherein said needle has an inner diameter of from about 0.1 to about 2 mm.

9. The method of claim 1, wherein said electrospinnable polymer is selected from the group consisting of polyamides, poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactides, polyglycolides, poly (lactide-co-glycolides), polyanhydrides, polyorthoesters, Poly(carbonate), poly(acrylo nitrile), poly(ethylene oxide), polyaniline, polyvinyl carbazole, polystyrene, poly(vinyl phenol), polyhydroxyacids, poly(caprolactone), polyanhydrides, polyhydroxyalkanoates, polyurethanes, collagen, albumin, alginate, chitosan, starch, hyaluronic acid, and blends and copolymers thereof.

10. The method of claim 1, wherein said electrospinnable polymer comprises polyvinyl alcohol.

11. The method of claim 1, wherein said applying an electrostatic field comprises inserting a first electrode in said spinneret, positioning a counterelectrode at a distance from said first electrode and applying a voltage current from 1 kV up to 30 kV between said first electrode and said counterelectrode.

12. The method of claim 11, wherein said distance is up to about 20 cm.

13. The method of claim 11, wherein said first electrode is formed from copper and said counterelectrode is formed from aluminum.

14. The method of claim 11, wherein said counterelectrode is a collector for said fibers.

15. The method of claim 14, wherein said collector is a rotating disc.

16. The method of claim 15, wherein said disc is provided with a tapered edge.

17. The method of claim 15, wherein said disc is further provided with a collecting table configured to rotate about the z-axis, the method further comprising the step of periodically rotating said table by a predetermined number of degrees about the z-axis, wherein a mat comprising layers of fibers is formed.

18. The method of claim 1, wherein said applying an electrostatic field comprises inserting a first electrode in said spinneret, positioning a counterelectrode at a distance from said first electrode and applying a voltage current about 30 kV between said first electrode and said counterelectrode.

19. A fibrous material encapsulating bacteria or non-filamentous viruses in viable form, wherein said fibrous material is formed by the method of claim 1, wherein said osmolarity regulating agent is comprised in said bacteria at a concentration which reduces dehydration of said microorganisms during electrospinning as compared to dehydration of said microorganisms dun electro in the absence said osmolarity regulating agent.

20. The fibrous material of claim 19, wherein said bacteria or said non-filamentous viruses exhibits increased viability as compared to said bacteria or said non-filamentous viruses subjected to electrospinning with an identical electrospinnable polymer in the absence of said osmolarity-regulating agent.

21. A fibrous material encapsulating non-filamentous viruses in viable form, comprising a plurality of fibers for encapsulating the viruses, each fiber comprising a polymer, an osmolarity regulating agent at a concentration which reduces dehydration of said non-filamentous viruses during electrospinning wherein the osmolarity regulating agent is 5% to 10% glycerol, and a non-filamentous virus.

22. The fibrous material of claim 21, wherein said non-filamentous viruses exhibits increased viability as compared to said non-filamentous viruses comprised in a fiber comprising said polymer and said non-filamentous viruses in the absence of said osmolarity-regulating agent.

23. The fibrous material of claim 22, wherein said viability of said non-filamentous viruses is determined by plaque forming ability.

24. A method of treating a bacterial or fungal infection of a subject, comprising applying the fibrous material of claim 21 to a wound or an external body surface infected with bacteria or fungus, wherein said fibrous material comprises said non-filamentous virus, and wherein said non-filamentous virus is capable of treating said bacterial or fungal infection, thereby treating the bacterial or fungal infection of the subject.

25. A method of killing bacterial pathogen of an animal subject, comprising mixing the fibrous material of claim 21 with foodstuff of the animal subject, wherein said fibrous material comprises said non-filamentous virus, and wherein said non-filamentous virus is capable of treating said bacterial or fungal infection of the animal subject, thereby killing bacterial pathogen of an animal subject.

* * * * *